(12) United States Patent
Jäggi

(10) Patent No.: US 6,425,871 B1
(45) Date of Patent: Jul. 30, 2002

(54) PUNCTURING DEVICE FOR TOMOGRAPHY

(75) Inventor: Kurt Jäggi, Bern (CH)

(73) Assignee: Tomo-Vision GmbH, Kehrsatz (CH)

( * ) Notice: Subject to any disclaimer, the term of this patent is extended or adjusted under 35 U.S.C. 154(b) by 0 days.

(21) Appl. No.: 09/700,050

(22) PCT Filed: Mar. 4, 1999

(86) PCT No.: PCT/CH99/00103
§ 371 (c)(1),
(2), (4) Date: Nov. 10, 2000

(87) PCT Pub. No.: WO99/58069
PCT Pub. Date: Nov. 18, 1999

(30) Foreign Application Priority Data

May 13, 1998 (CH) .............................. 1066/98

(51) Int. Cl.[7] .................................................. A61B 5/00
(52) U.S. Cl. ...................................................... 600/461
(58) Field of Search ................................ 600/459, 461, 600/462, 464

(56) References Cited

U.S. PATENT DOCUMENTS

| 4,826,487 A | 5/1989 | Winter ........................ 604/175 |
| 5,178,146 A | 1/1993 | Giese ....................... 128/653.2 |
| 5,394,457 A * | 2/1995 | Leibinger et al. ........... 378/162 |
| 5,961,455 A * | 10/1999 | Daum et al. ................. 600/407 |

FOREIGN PATENT DOCUMENTS

| DE | 19627314 | 4/1998 |
| EP | 0422369 | 4/1991 |
| EP | 0640842 | 3/1995 |
| EP | 0832610 | 4/1998 |

OTHER PUBLICATIONS

Abstract of DE 19627314, esp@cenet database, Apr. 2, 1998.

* cited by examiner

Primary Examiner—Max Hindenburg
(74) Attorney, Agent, or Firm—Seed Intellectual Property Law Group PLLC

(57) ABSTRACT

A puncturing device that can be observed by means of tomography, such as MRI, which can be operated simply, safely and reliably. One embodiment of the invention includes a cuboid body containing a needle guide, which extends to a base area of the cuboid body. The base area is configured for placement on the skin of a patient. Marker bores disposed in the cuboid body and containing a contrast medium make it possible to precisely align the needle guide with a tomography picture plane in that the images of the bores have to assume a particular mutual configuration on a monitor. This allows a puncture needle used with the needle guide to be observed along its entire path on tomograms.

15 Claims, 7 Drawing Sheets

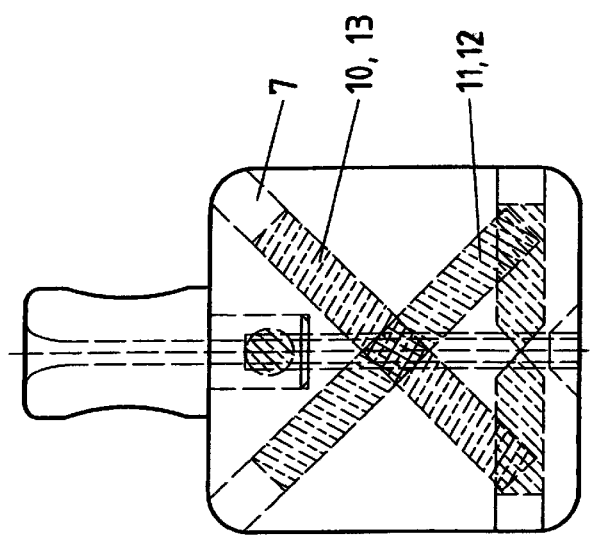
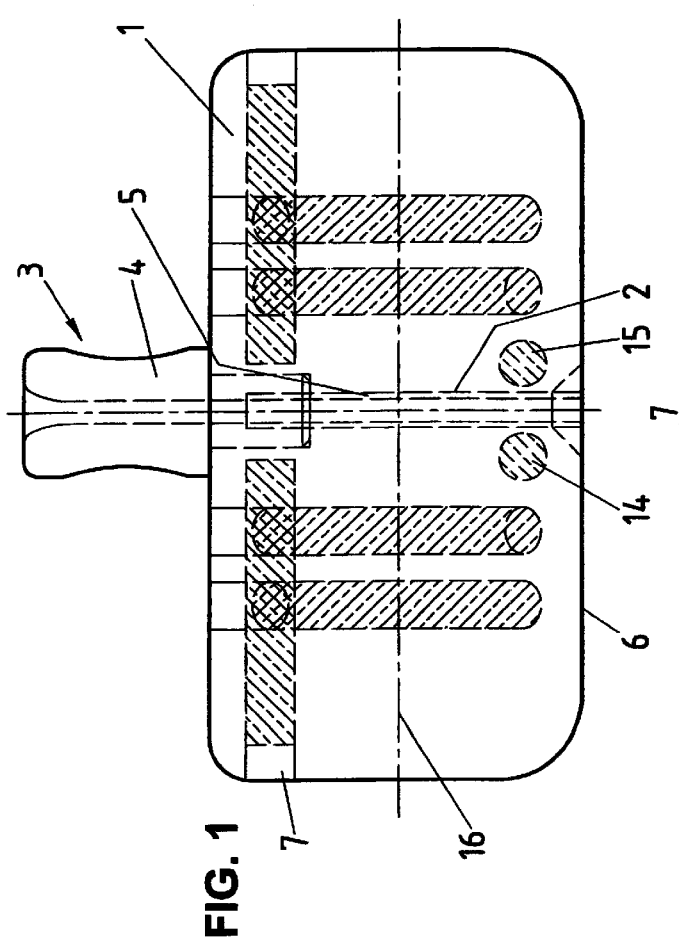
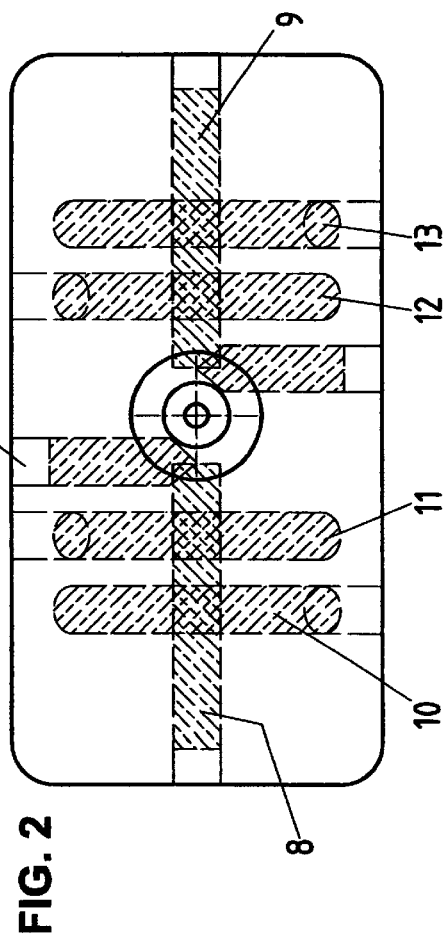
FIG. 1
FIG. 2
FIG. 3

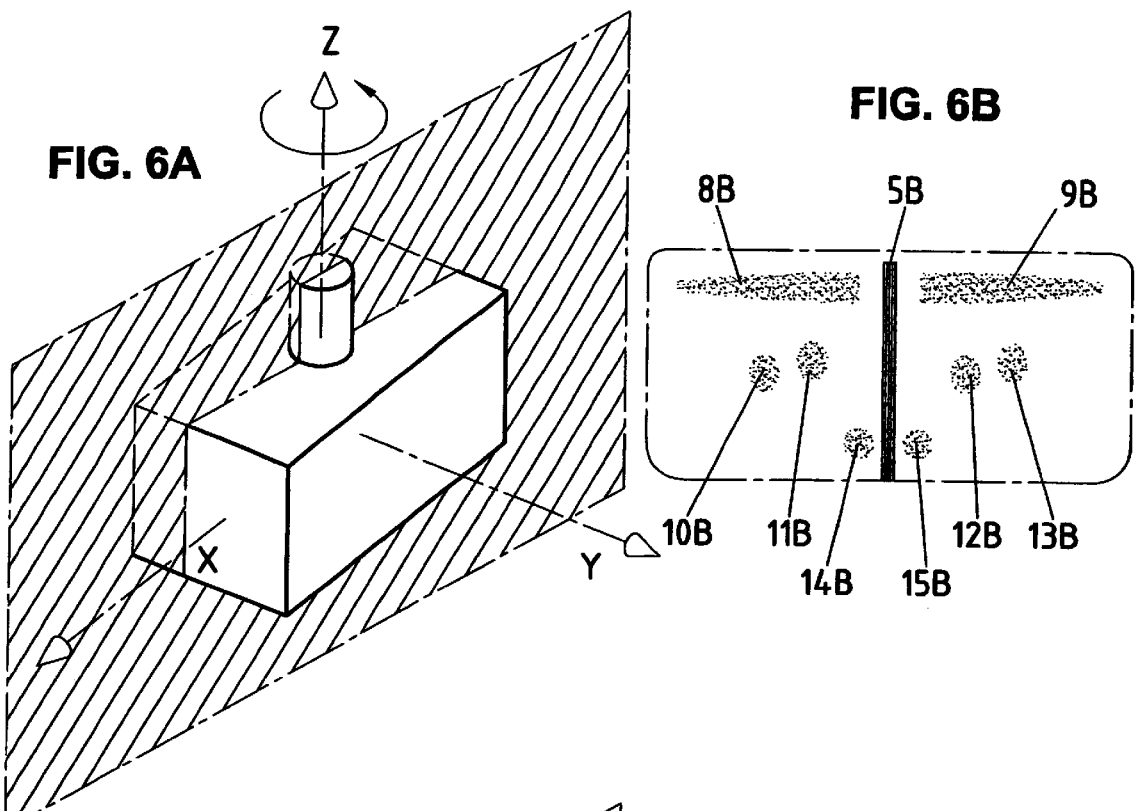
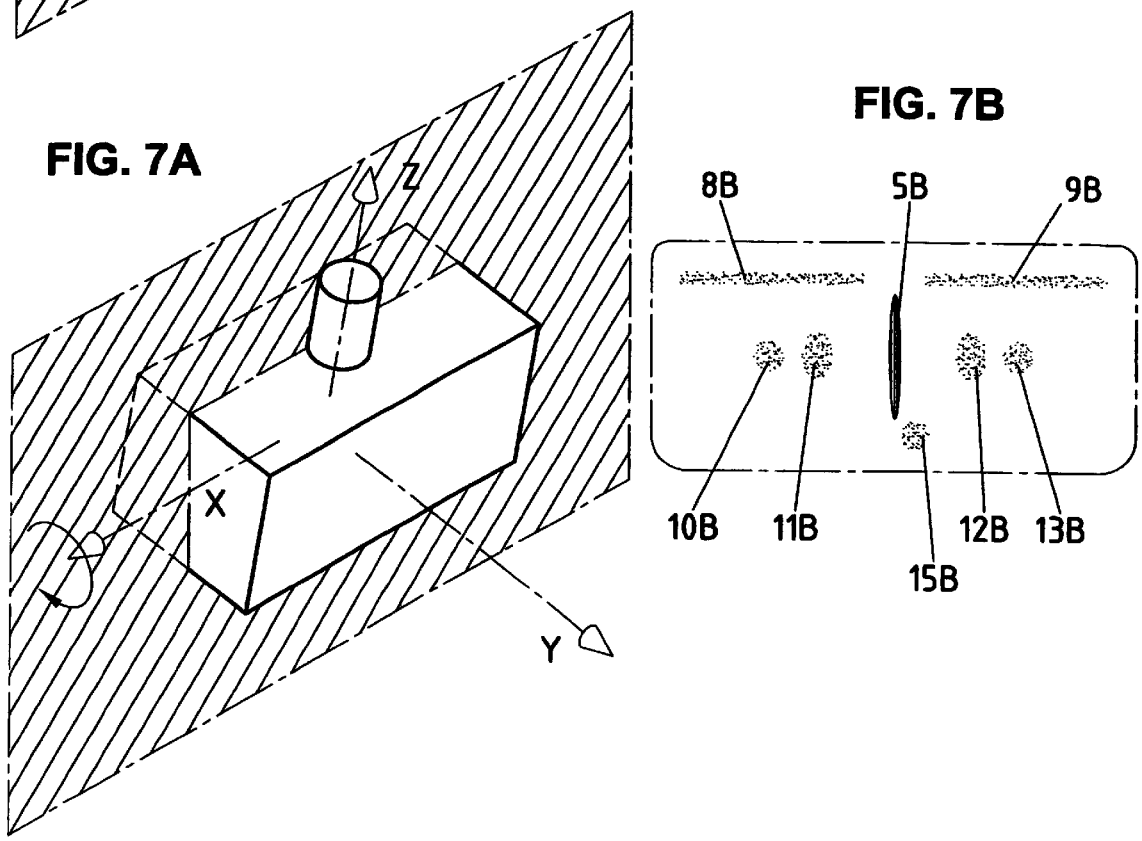

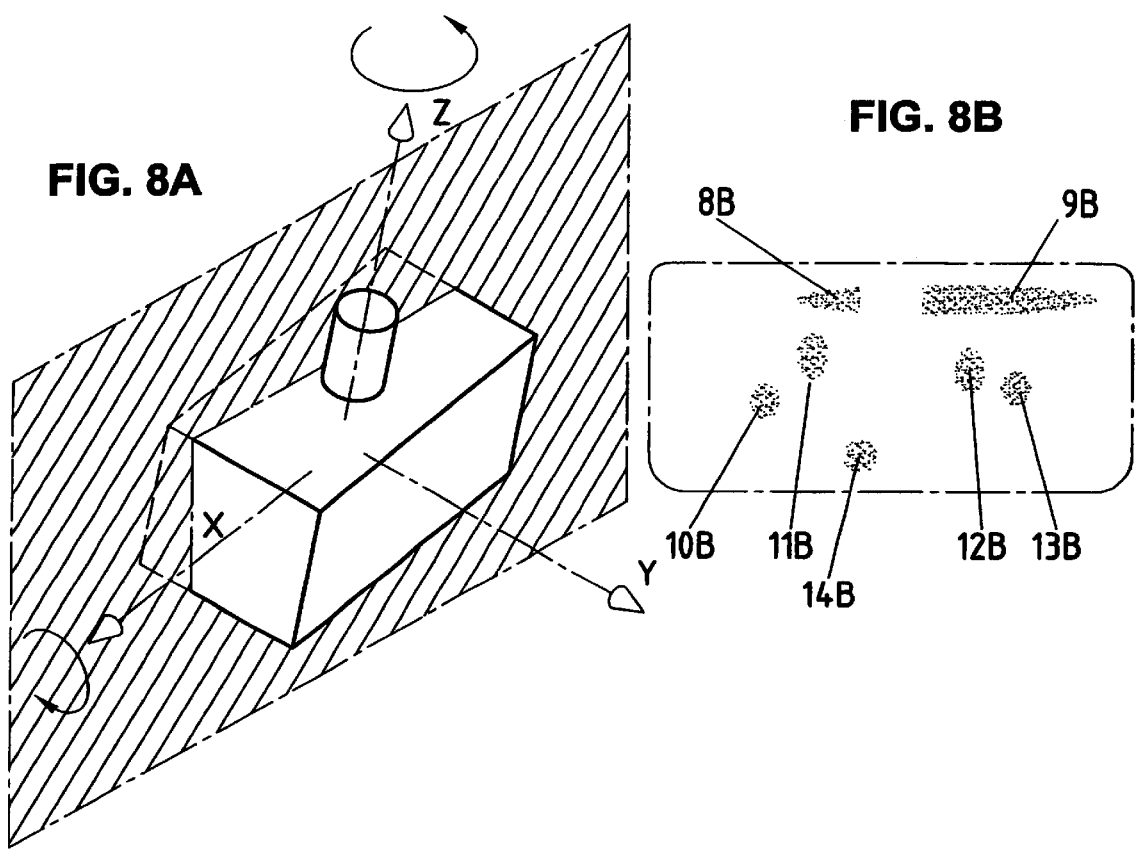

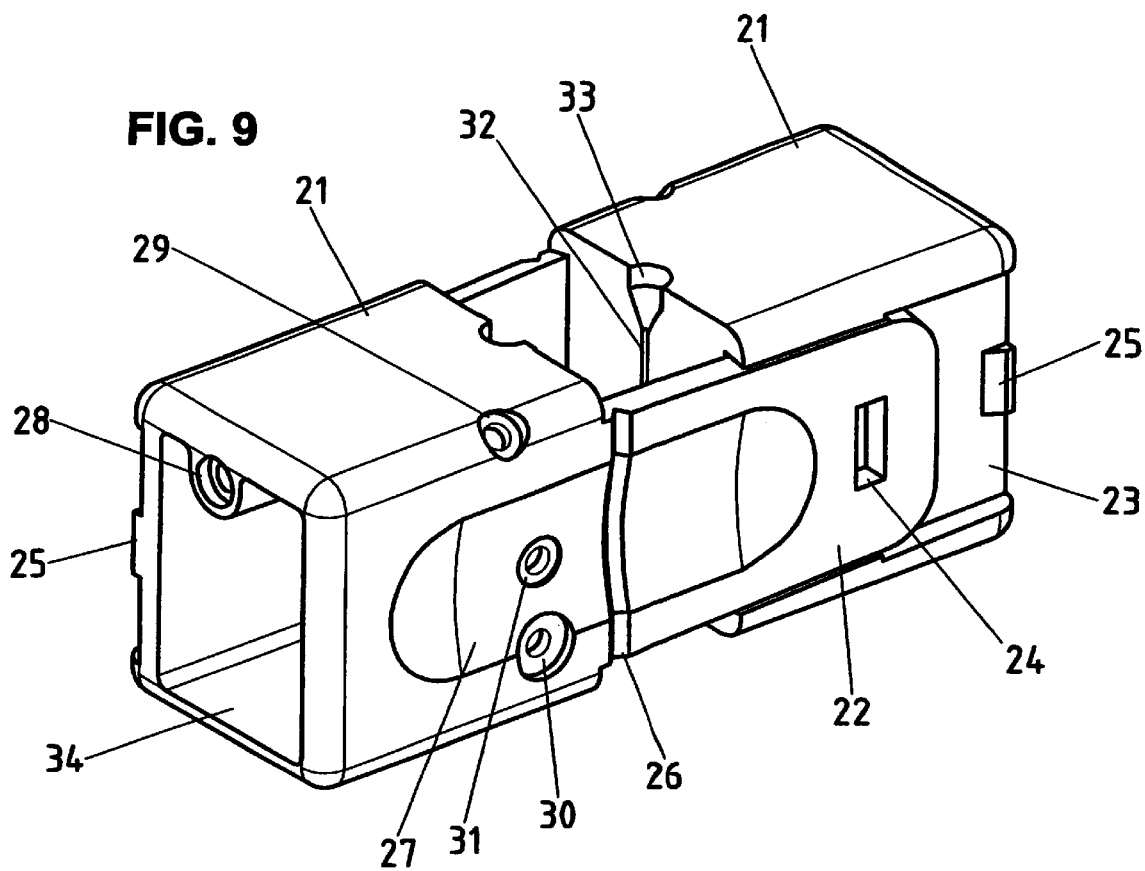
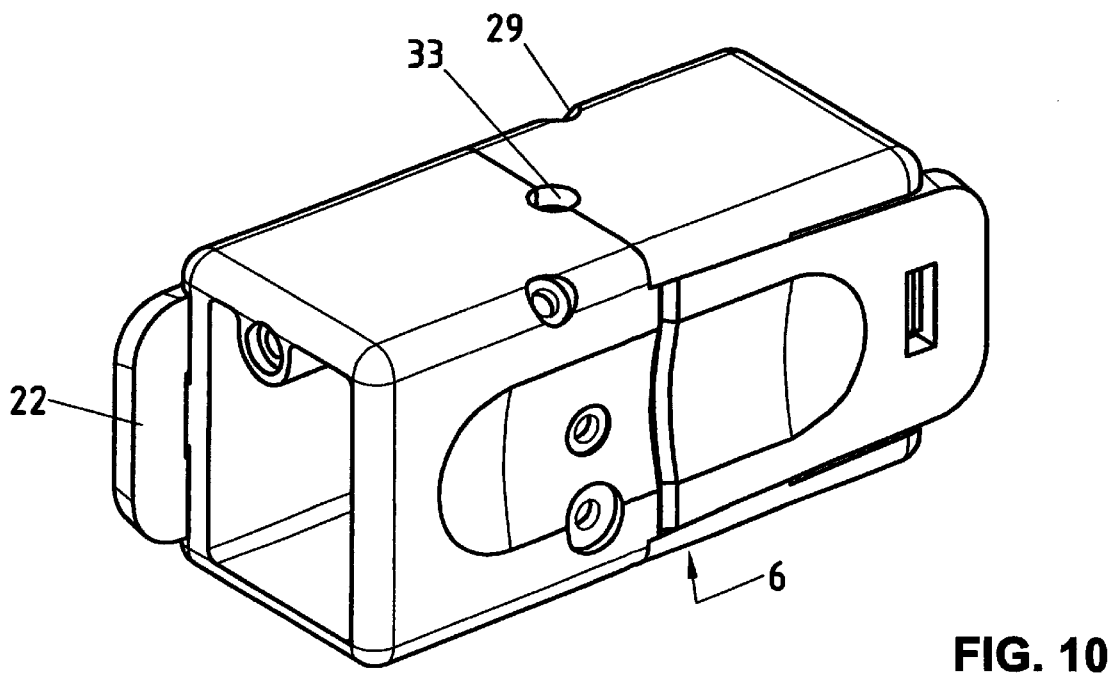

FIG. 11
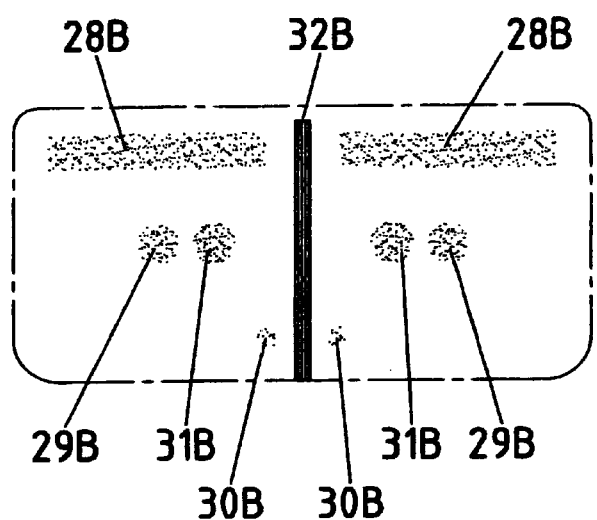
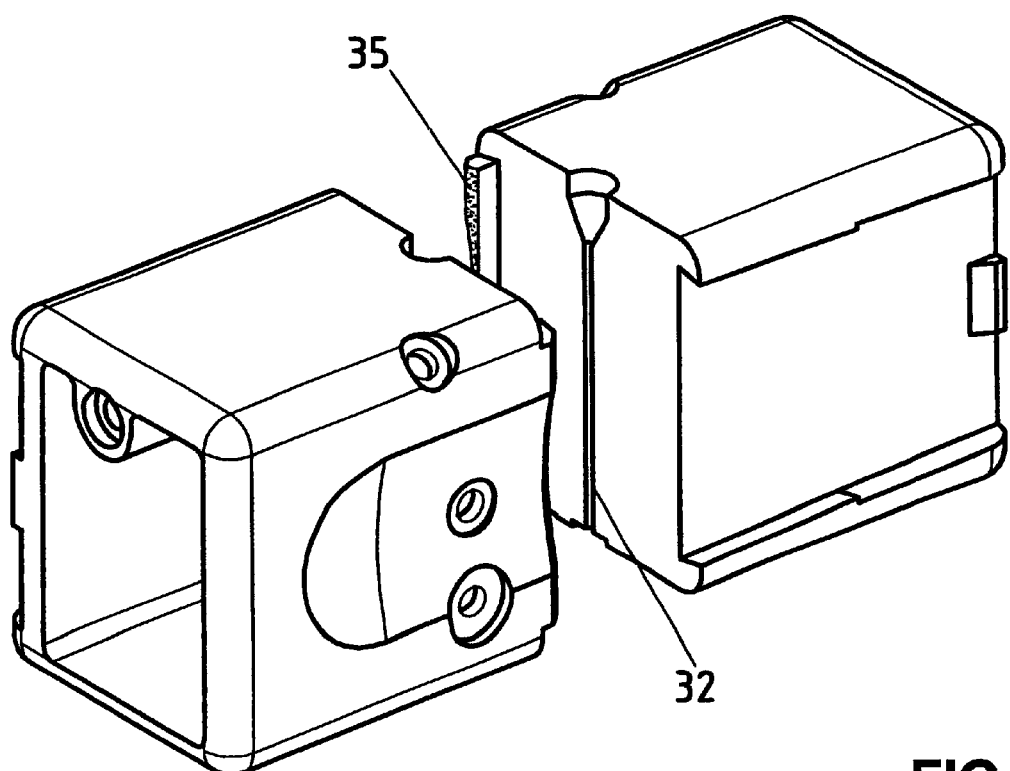
FIG. 12

PUNCTURING DEVICE FOR TOMOGRAPHY

BACKGROUND OF THE INVENTION

1. Field of the Invention

This invention relates to puncturing devices for tomography.

2. Description of the Related Art

Tomography, such as MRI (magnetic resonance imaging), operating in real time, and CT (computed tomography), is often used in imaging for medicine.

Understood by tomography in connection with the present invention should be imaging methods used in medicine, in particular MRI (magnetic resonance imaging), operating in real time, and CT (computed tomography).

Punctures monitored through tomography entail various problems and difficulties. The spatial relations in the imaging installation are very tight, whereby the dimensions of a puncturing device are limited. During MRI, not just any desired materials can be brought into the magnetic field, in particular no ferromagnetic materials. The physician follows the puncturing needle on the picture screen, and can only see this needle as long as it is located at least close to the cutting plane, which is determined in the case of MRI by the magnetic field, and in the case of CT by the X-rays. Thus it can very well happen that the puncture needle is visible in the region of the puncture site, but not its point, however, since its point is located in front of, or behind, the picture plane. It is easy to imagine the difficulties that confront the physician in such a situation. Upon puncturing of the puncture needle, in particular in the abdominal region of a patient, the tissue can first bend greatly inward, whereby a sighted organ to be punctured or a tumour can slip away sideways.

Various devices are known which serve the precise positioning of a patient in a tomographic installation, and which therefore also find application in punctures. Several of these devices operate with optical measurement of reference points placed on the body of the patient. These reference points can be markings drawn, pasted or also projected on the skin. The last-mentioned can be generated, for example, by means of a laser beam. All these optical devices have in common that they are very consuming and therefore expensive. Moreover, their dimensions and their arrangement in the tomographic installation can impede the physician during a puncture, or the physician can disturb the functioning of the positioning device if he inadvertently interrupts the measuring beams. A simple and precise way of guiding the needle is not available in any of the devices of this kind.

The printed patent specification U.S. Pat No. 4,826,487 relates to an alignment button for a stereotaxic plug and method of using the same. The plug can bear a thread on its outer circumference, and is intended to be placed in the cranium of a patient. It bears a plurality of axial bores disposed in a particular pattern, of which a first group is designed as a guide cannulae for surgical instruments. A second group of axial bores is designed as marker bores, the bores containing a contrast medium depending upon the respective tomography. Gold is proposed as the contrast medium for pictures with X-rays, and for MRI images water or lipids. After insertion of the plug, the scalp is pulled over it and sutured in order to keep the risk of infection as minimal as possible. The alignment button contains cannulae and marker bores disposed in a pattern identical to the pattern of the plug. It is precisely aligned with the plug in a corresponding imaging device, and then sewn to the scalp. With this system both an exact locating of the puncture site by means of a tomographic method as well as a precise guiding of a surgical instrument, for example a puncture needle, are possible. However, this system can only be used sensibly for surgical interventions repeated at temporal intervals, in particular in the skull, and is not suitable for single punctures. Indicated in the printed patent specification is that the alignment button can also be used alone. The guiding of the needle is thereby omitted, however, so that although the puncture site is determinable by means of the alignment button, the direction of puncture of the needle is not.

The printed patent specification U.S. Pat. No. 5,178,146 relates to a system for aligning a patient for use of MRI or other imaging methods. The system includes in particular a cuboidal box to be placed spaced apart from the region of the body of the patient to be examined, in the walls of which box tubes, filled with a contrast medium, have been placed in a particular pattern. Indicated as contrast medium for MRI is, for example, a gadolinium compound, and for CT, a barium compound. Both tubes disposed in a right-angle pattern as well as tubes disposed running diagonally are provided. The latter generate shadows in the picture which displace themselves in the picture plane when the box is moved through the field. From the mutual position of these shadows the physician can discern whether the patient has assumed the desired position in the imaging installation. This system is intended in particular to bring into line pictures generated by means of MRI with pictures generated by other means. For this purpose the contrast medium in the tubes is exchangeable. One application example is in radiation therapy in which, for example, a tumour is first located by means of MRI, and subsequently irradiated with X-rays. The precise position for irradiation is then reached when the pattern generated by the tubes on the CT picture coincides with that on the previously generated MRI picture. Although it is mentioned in the printed patent specification that the system can also find application for punctures, there are no indications of a needle guide. Above and beyond that, it is apparent that the said box can additionally impede the doctor when puncturing.

BRIEF SUMMARY OF THE INVENTION

It is the objective of the present invention to create a puncturing device which can be manufactured simply and inexpensively, and can be operated safely and reliably. Another objective of the invention is to provide a puncturing device with small dimensions, and which therefore is usable with the narrow space relations that prevail in the imaging installation. A further objective of the invention consists in creating a puncturing device which can be made of materials that cause no interference during the respective tomographic procedure. Furthermore the invention has the objective of providing the physician with a puncturing device with which the puncture needle can be aligned precisely with the picture plane, so that this needle can be observed at any time on the picture screen from the puncture site to the point. Finally, with the puncturing device according to the invention the respective bodily region of the patient should be able to be compressed before insertion of the puncture needle, so that the indentation of this region and thereby a slipping away of the organ or tumour to be punctured can be minimized. These objectives are achieved through the present invention.

In some embodiments of the present invention, a puncturing device is provided that comprises a body with substantially the shape of a cuboid having a base area parallel to a longitudinal axis of the body. The base area is configured to be placed upon the skin of a patient. A guide means cuts the base area at a right angle, and there are at least two elongated hollow spaces disposed at right angles to the longitudinal axis of the body, but not parallel to the guide means and not parallel to one another.

A further object of the invention consists in proposing a puncturing device which can be removed after insertion of the puncture needle into the body of a patient, without the puncture needle having to be pulled out for this purpose. This object is achieved through a puncturing device having the features of claim 7.

Further special embodiments of the puncturing device according to the invention are described in the dependent claims.

The invention will be described more closely in the following with reference to the embodiments presented in the drawings.

BRIEF DESCRIPTION OF THE SEVERAL VIEWS OF THE DRAWING(S)

FIG. 1 is an enlarged elevation view showing an embodiment of the puncturing device according to the present invention.

FIG. 2 is a top view of the embodiment of the present invention according to FIG. 1.

FIG. 3 is a side elevation view of the embodiment of the present invention according to FIG. 1.

FIG. 6A is a perspective view of a puncturing device according to FIG. 1, which is disposed in the picture plane rotated about a vertical axis.

FIG. 6B is a tomogram, represented schematically, of the device disposed according to FIG. 6A.

FIG. 7A is a perspective view of a puncturing device according to FIG. 1, which is disposed in the picture plane rotated about a horizontal axis.

FIG. 7B is a tomogram, represented schematically, of the device disposed according to FIG. 7A.

FIG. 8A is a perspective view of a puncturing device according to FIG. 1, which is disposed in the picture plane rotated about a horizontal and a vertical axis.

FIG. 8B is a tomogram, represented schematically, of the device disposed according to FIG. 8A.

FIG. 9 is a perspective view of another embodiment of the puncturing device according to the present invention, comprising two identical parts, manufactured by injection moulding, which are in the process of being joined together.

FIG. 10 is the embodiment according to FIG. 9 in completely assembled, ready-to-use state.

FIG. 11 is a tomogram, represented schematically, of the device according to FIG. 10 with correct alignment.

FIG. 12 is the embodiment according to FIG. 9, after use, in a separated state.

DETAILED DESCRIPTION OF THE INVENTION

Figure 4A:
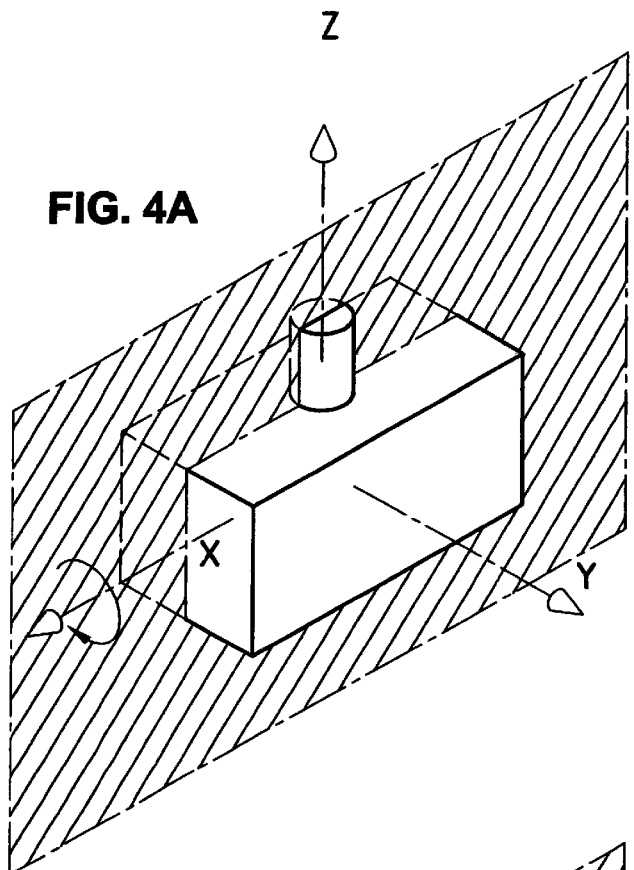
FIG. 4A is a perspective view of a correctly aligned puncturing device according to FIG. 1.

FIGS. 1 to 3 show an embodiment of the puncturing device according to the invention. A cuboid 1 with rounded edges, which comprises synthetic material, forms the main part of the device. A guide bore 2, continuous from top to bottom—in the position for use—serves to accept a needle guide 3, which includes a handle 4 and a guide tube 5 firmly connected thereto. In some embodiments the handle is a synthetic material and the guide tube is titanium. The needle guide 3 in this embodiment can be a disposable part, and the handle 4 can be coloured so that it is discernable at first glance which needle diameter the needle guide is configured for. As can be seen clearly in FIG. 1, the guide tube extends to the contact surface 6 of the cuboid 1, which can be placed upon the skin of a patient.

Present in the cuboid are a plurality of marker bores, represented in FIGS. 1 to 3 by broken lines. In the present example they are designed as blind-hole bores, filled with a contrast medium and closed by stoppers 7. Used as contrast medium can be the substances known from the state of the art used for this purpose. For MRI purposes, the following mixture has proved to be especially good: lobitridol (or other iodine RKM), gadopentetate dimeglumine, methylhydroxy-ethyl-cellulose and water. The gadolinium concentrate range should be thereby selected from between 0.5 mM and 40 mM, whereby the optimal range lies close to 1 mM. Furthermore practice has shown that during CT, air can also be used as the contrast medium. In the perpendicular, longitudinal central plane of the cuboid, there are marker bores 8 and 9, which, from opposite sides, extend into the vicinity of the needle guide 3. Further marker bores 10 to 13 lie in parallel planes, perpendicular to the said perpendicular longitudinal central plane, and project from the upper edge regions diagonally into the interior of the cuboid. Finally, two more marker bores 14 and 15 are provided, conically pointed at their inner-lying end, which bores, coming from opposite sides, extend parallel, spaced with respect to one another, and at the same distance from the contact surface 6, perpendicular up to the longitudinal central plane. The bores crossing one another 10 and 11, respectively 12 and 13, can also cut in pairs.

In the following it will be shown, with reference to the drawing FIGS. 4 to 8, how the device described above is used. Assumed is that the physician wants to puncture an organ in the abdomen of a patient with the aid of an MRI device. The puncturing device according to the invention is suitable both for short, closed as well as for open MRI systems. After the physician has decided upon a needle diameter, for example 1.2 mm, a corresponding, sterilised cuboid 1 is prepared, whose guide bore 2 has a diameter of, for example, 1.6 mm. A needle guide 3 is taken from a sterile package, and is inserted into the guide bore 2. To prevent contamination of the opening of the needle guide, this can be sealed, for example with a little rod of synthetic material, which is pulled out on the side of the contact surface 6 after insertion of the needle guide 3.

After the organ has been located, the puncturing device, that is the cuboid 1 with inserted needle guide 3, is placed with the contact surface 6 on the abdominal wall of the patient. As soon as the cuboid comes into the operating range of the MRI, the marker bores are discernible as shadows on the picture screen. These shadows are designated in FIGS. 4B to 8B by the reference symbols of the corresponding marker bores, respectively of the guide tube, supplemented by a "B". The puncturing device has attained the correct alignment shown in FIG. 4A, if a picture corresponding to FIG. 4B appears on the monitor. Understood by "correct" in this context is that the needle guide is situated precisely in the picture plane and thus it is ensured that, with unchanged position, the puncture needle can be observed on the monitor along its entire route. It is also to be mentioned here that in particular with MRI the area represented is actually not a plane, but rather a layer with a thickness of 3 to 6 mm. In FIG. 4B, the little guide tube 5, made of titanium, of the needle guide 3 <is> to be recognised along its entire length. The marker bores 8 and 9 appear as lines of even width 8B and 9B, and the marker bores 10 to 13 generate oval dots 10B to 13B, all of which are situated on a horizontal straight line. Finally, the marker bores 14 and 15 situated in the vicinity of the contact surface 6 are to be recognised as dots of equal size 14B and 15B.

Shown in FIGS. 5 to 8 are views which the physician could be given if the puncturing device is not exactly aligned with the respect to the picture screen. FIG. 5B shows a picture of the position illustrated in FIG. 5A in which the device is situated in front of the picture plane. The images of the guide tube 5 and of the marker bore 15 are not present in this figure because these parts are located in front of the picture plane. From the narrow, but evenly thick lines 8B and 9B, it can be deduced that the cuboid is oriented parallel to the picture plane. Both from the ovals 10B to 13B, which are not situated on a straight line, but are shifted vertical toward one other, as well as from the absence of an image of the marker bore 15, one can see that the cuboid has to be pushed away from the observer, so that its middle plane is aligned with the picture plane. Although the needle guide 3 is located precisely in the picture plane in FIGS. 6A and 6B, the puncturing device is nevertheless rotated about the axis of the needle guide. This is to be recognised from the irregularly thick lines 8B and 9B, and also from the dots 10B to 13B, not aligned on a straight line, and also from the dots 14B and 15B, whose diameter should be smaller. According to FIGS. 7A and 7B, the puncturing device is rotated about an axis X parallel to the picture plane and at a right angle to the needle guide. The dots 10B to 13B are nevertheless aligned in a straight line, from which it can be concluded that the region of the longitudinal middle axis of the cuboid lies in the picture plane; however, it can be clearly seen that not all these dots have the same shape, which indicates a rotation of the cuboid about this very longitudinal middle axis. This is to be seen, by the way, also from the fact that only one image 5B of the guide tube 5, of the middle region, is visible. Finally the absence of the image of the marker bore 14 indicates that the region of the cuboid near the contact surface 6 lies behind the picture plane. From this it is also immediately clear to the doctor in which direction the correction must take place. Finally, FIGS. 8A and 8B show still another position of the puncturing device, in which the wrong positions shown in FIGS. 6A, 6B, 7A and 7B are combined. The position of the dots 10B to 13B indicates that the cuboid is further removed from the correct position to the left than to the right, it being recognisable from dot 14B that the left region apparently lies in front of the picture plane. Consequently the physician will first rotate the left region of the device in the direction of the picture plane, after which the picture will appear approximately as shown in FIG. 7B; from this position then a rotation about the X axis suffices, whereby the upper region of the device is turned toward the picture plane in order to achieve the picture shown in FIG. 4B and thereby a precise alignment of the device.

Figure 4B:
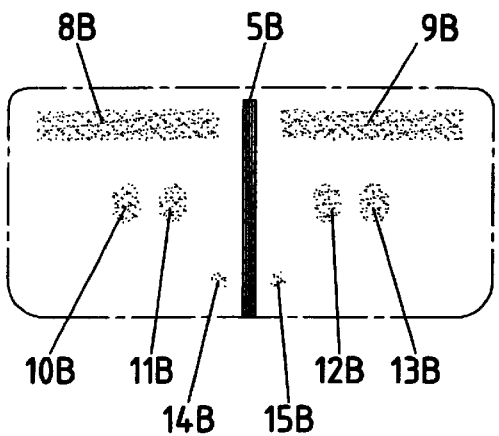
FIG. 4B is a tomogram, represented schematically, of the device aligned according to FIG. 4A.
Figure 5A:
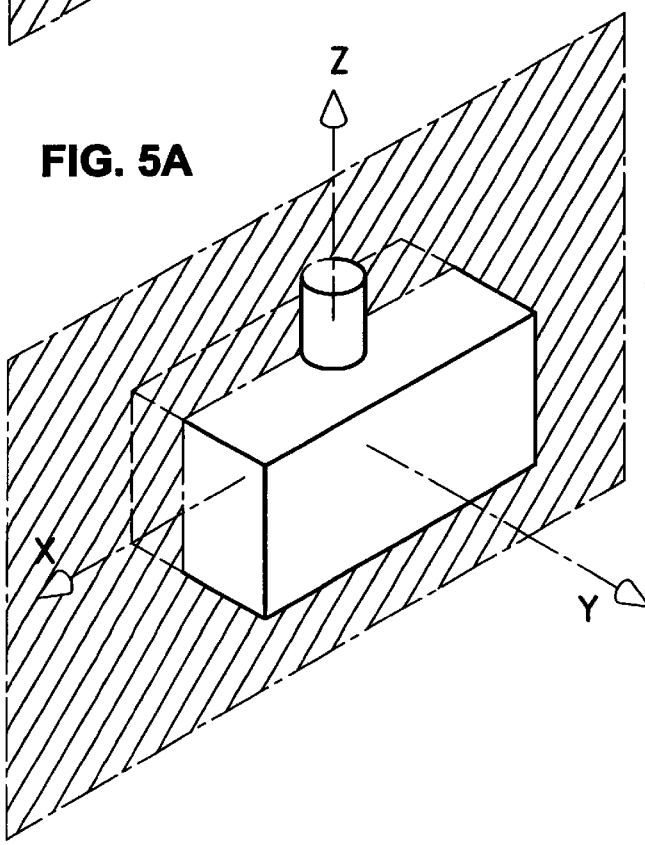
FIG. 5A is a perspective view of a puncturing device according to FIG. 1, which is shifted parallel with respect to the picture plane.
Figure 5B:
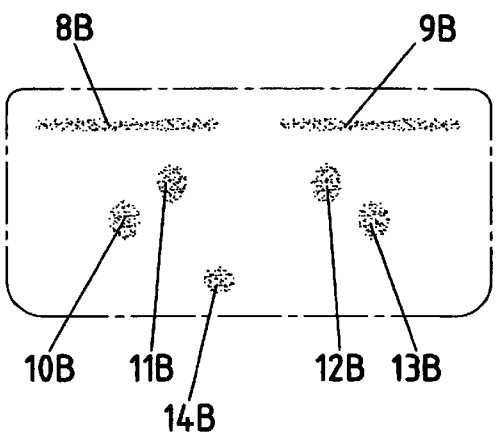
FIG. 5B is a tomogram, represented schematically, of the device disposed according to FIG. 5A.

As soon as the puncturing device is oriented according to FIGS. 4A and 4B, and of course also the site to be punctured is aligned with the picture plane, the puncture needle is inserted into the needle guide 3. For this purpose the latter has a conically widened opening at its upper end. Before the doctor inserts the puncture needle into the body of the patient, he compresses the respective bodily region in that he presses the puncturing device against the abdominal wall. The risk of a slipping away of the respective organ during the subsequent penetration of the needle is thereby considerably reduced. Furthermore by means of this step, the entire device comes closer to the organ to be punctured, and can therefore be aligned therewith even more precisely. Since the guide tube 5 of the needle guide 3 extends to the skin of the patient, the puncture takes place exactly at the desired place. Thanks to the fact that the puncture direction of the puncture needle is guided precisely by means of the device according to the invention, the needle's path can be followed on the monitor and watched closely, and the puncture can be carried out exactly at the desired place.

After the operation, the needle guide 3 is removed from the cuboid 1, and is disposed of. The cuboid is sterilised and made ready for reuse, a cold sterilisation method having to be employed when the contrast medium in the marker bores is fluid.

The second embodiment example shown in a perspectival view in FIG. 9 is intended for one-time use, and consists of two identical parts 21 produced from a synthetic material by means of injection moulding. These parts 21 are constructed such that they can be joined in the position shown in FIG. 9 and then form a cuboid, which corresponds to the cuboid 1 of FIGS. 1 to 3. When joining the two parts 21, a tab 22 of each part slides into a guide 23 on the other part in each case, until the front edge of the tab is slightly lifted by means of an activity of a locking projection 25. Upon further pushing together of the two identical parts, the locking projection 25 comes into the region of a recess 24 provided in the tab, so that the tab springs back from its raised position and the locking projection 25 is accepted in the recess 24. This end position, in which the parts 21 form a body corresponding to the cuboid of FIGS. 1 to 3, is shown in FIG. 10. A recessed grip 27 is provided in the side faces of the parts 21 for better handling of the cuboid by the physician.

The cuboid formed by the parts 21 also has marker bores. The marker bore 28 corresponds thereby to the marker bores 8 and 9 of the embodiment according to FIGS. 1 to 3, the marker bore 29 corresponds to the marker bores 10 and 12 of FIGS. 1 to 3, and the marker bore 30 is, like the marker bores 14 and 15 of FIGS. 1 to 3, conically pointed at its inner-lying end. The marker bore 31, lying in a horizontal plane, replaces the marker bores 11 and 13 of the embodiment example according to FIGS. 1 to 3. The guide bore 32 has a smaller diameter than the guide bore 2 according to FIGS. 1 to 3 because in this embodiment example the needle guide 3 is done away with, and the puncture needle is thus guided directly in the cuboid. For easier insertion of the puncture needle, a countersink 33 is provided on the upper end of the guide bore 32. The hollow space 34 visible on the left side of FIGS. 9, 10 and 12, is construction-related since, as is well known, pieces which are manufactured by injection moulding must have wall thicknesses which are as regular as possible. This is of no significance for the functioning of the device, however.

FIG. 11 shows schematically, in a way similar to FIG. 4B, a tomogram of the device according to FIG. 10 with correct alignment. The marker bores 29 running slanted in the cuboid with respect to the supporting surface are visible as shadows 29B, which move upward and downward in the picture when the cuboid is pushed transversely to the picture plane. The marker bores 31 running parallel to the supporting surface generate shadows 31B on the picture which remain at the same place during a movement of the cuboid transversely to the picture plane. Thus the puncturing device is aligned exactly in the picture plane when the dots 29B and 31B are disposed on the picture along a straight line, the areas 28B are visible, and the dots 30B are equally large. So that the dots 29B, formed through the bores 29 running slanted, appear round, the bores 29 in this example are designed in the shape of an ellipse, whose longer axis is disposed parallel to the base area.

As already mentioned, the puncturing device according to FIGS. 9 to 12 is conceived for one-time use. For this purpose it is delivered in the state shown in FIG. 10, packed in a sterile way. As soon as the point of the puncture needle has reached its target in the body of the patient, the task of the cuboid is fulfilled. The cuboid can now impede the physician during further manipulations of the puncture needle, and removing it, therefore, is desired. For this purpose the cuboid consists of the two said parts 21, which are separated from one another after use. To achieve this, the doctor bends the tabs 22 outward in order to bring out of engagement the recesses 24 and the locking projections 25. A nick 26 is provided on the tab 22, which causes the tab to break off when bent outward. A reuse of the no longer sterile device is thereby prevented. FIG. 12 shows the two separated parts with the resultant breaking area 35 in the region of the nick. The tab 22 and the nick 26 are dimensioned such that the tab does not break during assembly of the two parts 21. If necessary, for assembly, the parts can be slightly heated.

Figure 13:
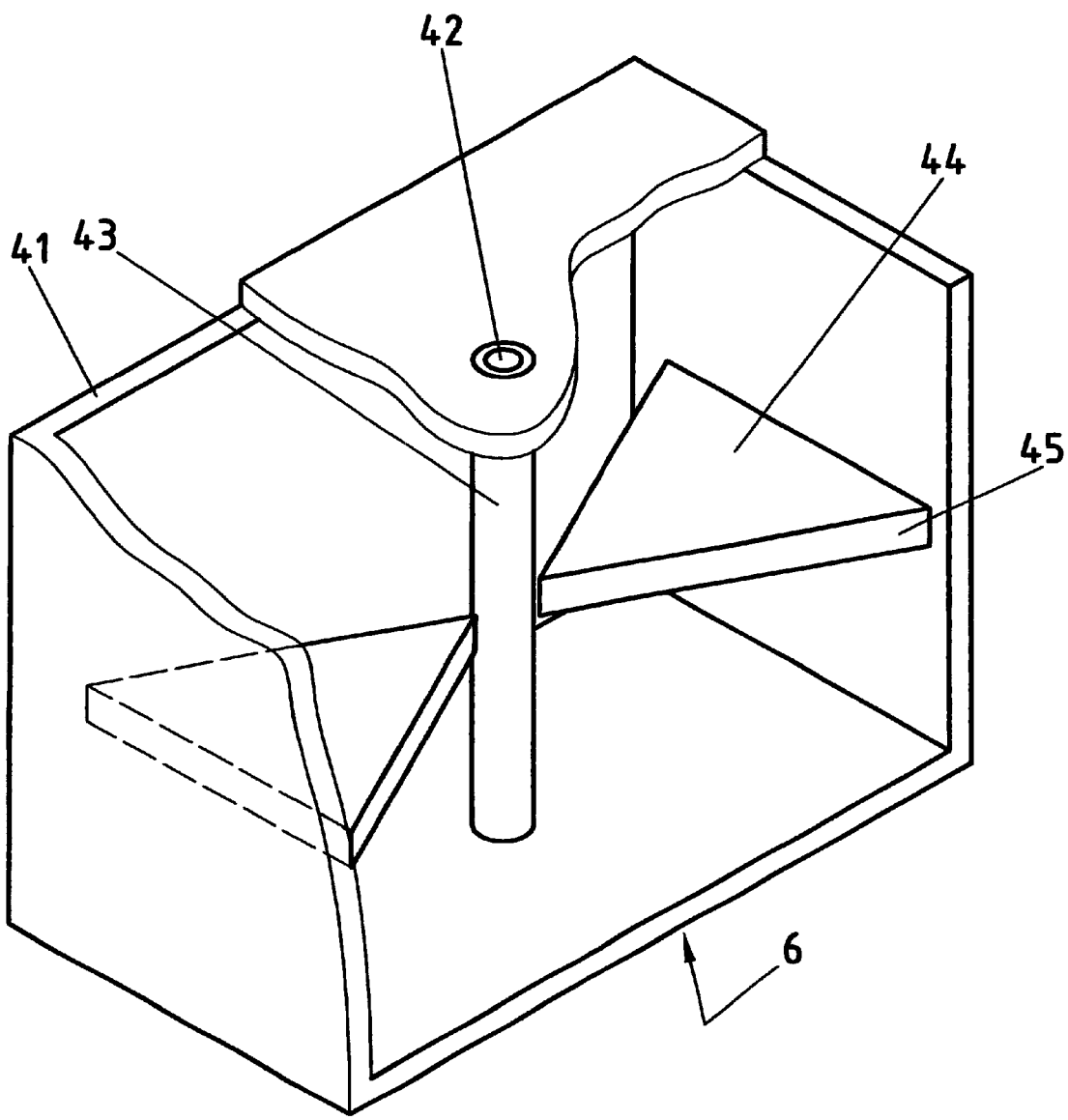
FIG. 13 is another embodiment of the puncturing device according to the present invention.

Shown in FIG. 13, in perspective and partially cut open, is a further, alternative design of the puncturing device according to the invention. The principle described in the foregoing is reversed here in that the cuboid 41 is designed substantially hollow and is filled with contrast medium. The guide bore 42 for the puncture needle is located in a guide tube 43 which passes through the hollow cuboid. Connected to both end walls of the cuboid is one alignment body 44 each, which serves to align the device with the picture plane. Each alignment body 44 tapers in the direction toward the guide bore, so that its lateral peripheries 45 are designed elongated and are disposed not parallel to the guide means and not parallel to one another. In operation, a similar effect thereby results as with the previously described embodiments. The more the central plane of the cuboid, in which the guide bore 42 is located, approaches the picture plane, the longer the shadows formed by the alignment body 44 become, which extend from the end faces of the cuboid in the direction toward the guide bore. In this embodiment further guide bodies can also be provided of course, which aid the precise positioning of the cuboid in the picture plane. These alignment bodies can be disposed in a way similar to the marker bores of the previously described embodiment examples, only bores are not involved here, but bodies which extend from the walls of the hollow cuboid into its interior.

What is claimed is:

1. A puncturing device for aligning a puncture needle with a tomography picture plane, comprising:
   a body, substantially cuboid in shape, having a base area parallel to a longitudinal axis of the body;
   a guide means, for the puncture needle, disposed in the body wherein an axis of the guide means cuts the base area at a right angle; and
   a plurality of elongated hollow spaces containing contrast medium disposed in the body, wherein at least two of the elongated hollow spaces are at a right angle to the longitudinal axis of the body, but not parallel to the guide means, and not parallel to one another.

2. The puncturing device according to claim 1, wherein two of the elongated hollow spaces are at a right angle to the longitudinal axis of the body but not parallel to the guide means and not parallel to one another, and are located on opposite sides of the guide means.

3. The puncturing device according to claim 1 or 2, wherein:
   at least one of the elongated hollow spaces extends from an end face of the cuboid body into the vicinity of the guide means, in a plane defined by the longitudinal axis of the body and the axis of the guide means; and
   at least another of the elongated hollow spaces extends from another face of the cuboid body into the vicinity of the guide means, in the plane defined by the longitudinal axis of the body and the axis of the guide means.

4. The puncturing device according to claim 3, wherein:
   at least one of the elongated hollow spaces extends from a side face of the cuboid body into the vicinity of the guide means, at a right angle to the plane defined by the longitudinal axis of the body and the axis of the guide means; and
   at least another of the elongated hollow spaces extends from another side face of the cuboid body into the vicinity of the guide means, at a right angle to the plane defined by the longitudinal axis of the body and the axis of the guide means.

5. The puncturing device according to claim 1 or 2, wherein:
   at least one of the elongated hollow spaces extends from a side face of the cuboid body into the vicinity of the guide means, at a right angle to a plane defined by the longitudinal axis of the body and the axis of the guide means; and
   at least another of the elongated hollow spaces extends from another side face of the cuboid body into the vicinity of the guide means, at a right angle to the plane defined by the longitudinal axis of the body and the axis of the guide means.

6. The puncturing device according to claim 5, wherein:
   at least one of the elongated hollow spaces extends from an end face of the cuboid body into the vicinity of the guide means, in the plane defined by the longitudinal axis of the body and the axis of the guide means; and
   at least another of the elongated hollow spaces extends from another end face of the cuboid body into the vicinity of the guide means, in the plane defined by the longitudinal axis of the body and the axis of the guide means.

7. The puncturing device according to claim 1, wherein the elongated hollow spaces are blind bores whose outerlying end is closed.

8. The puncturing device according to claim 1, wherein the guide means further comprises a guide tube removably inserted in a guide bore, the guide tube having a handle fastened to one end with a conical insertion opening for a puncture needle.

9. The puncturing device according to claim 1, wherein the body is separable into at least two parts in the region of the guide means such that the parts are removable from the puncture needle without the puncture needle having to be pulled back along its axis.

10. The puncturing device according to claim 9, wherein the separable parts of the body meet in a plane containing the guide means.

11. The puncturing device according to claim 10, wherein the separable parts of the body are held together by engagement means.

12. The puncturing device according to claim 11, wherein the engagement means are resilient tabs having locking projections which secure to the opposing separable part of the body.

13. The puncturing device according to claim 12, wherein the resilient tabs have break-off sites which break if the resilient tabs are bent for the purpose of releasing the locking projections.

14. The puncturing device according to claim 1 or 9, wherein the guide means comprise a guide boar, an end of the guide boar remote from the base area having a conical extension for easier insertion of the puncture needle.

15. A puncturing device for aligning a puncture needle with a tomography picture plane, comprising:

a hollow body, substantially cuboid in shape, having a base area parallel to a longitudinal axis of the body;

a guide means for the puncture needle, the guide means being disposed in the body and wherein the axis of the guide means cuts the base area at a right angle; and alignment bodies comprising contrast medium, disposed in the body, wherein the alignment bodies have elongated peripheries which are disposed not parallel to the guide means and not parallel to one another.

* * * * *